US012788842B2

(12) United States Patent
Haas et al.

(10) Patent No.: US 12,788,842 B2
(45) Date of Patent: Nov. 10, 2026

(54) OSTEOTROPIC BONE REPLACEMENT

(71) Applicants: Universität Heidelberg, Heidelberg (DE); Andreas Haas, Heidelberg (DE)

(72) Inventors: Andreas Haas, Heidelberg (DE); Christian Kasperk, Heidelberg (DE); Michael Burchard, Eberbach (DE)

(73) Assignees: Andreas Haas, Heidelberg (DE); Universitat Heidelberg, Heidelberg (DE)

( * ) Notice: Subject to any disclaimer, the term of this patent is extended or adjusted under 35 U.S.C. 154(b) by 1032 days.

(21) Appl. No.: 17/619,952

(22) PCT Filed: Aug. 14, 2020

(86) PCT No.: PCT/EP2020/072884

§ 371 (c)(1),
(2) Date: Dec. 16, 2021

(87) PCT Pub. No.: WO2021/032628

PCT Pub. Date: Feb. 25, 2021

(65) Prior Publication Data

US 2022/0370681 A1 Nov. 24, 2022

(30) Foreign Application Priority Data

Aug. 16, 2019 (EP) .................................... 19192028

(51) Int. Cl.
*A61L 27/12* (2006.01)
*C04B 35/447* (2006.01)

(52) U.S. Cl.
CPC ............ *A61L 27/12* (2013.01); *C04B 35/447* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 3,929,971 A | 12/1975 | Roy | |
| 4,938,938 A | 7/1990 | Ewers et al. | |
| 6,881,227 B2 * | 4/2005 | Jordanova-Spassova .................. | A61L 27/425 423/311 |
| 2012/0111226 A1 | 5/2012 | Bujoli et al. | |
| 2019/0008997 A1 | 1/2019 | Tampieri et al. | |

FOREIGN PATENT DOCUMENTS

| | | | |
|---|---|---|---|
| CN | 101928136 | A | 12/2010 |
| DE | 3542744 | C1 | 5/1987 |
| JP | H01502812 | A | 9/1989 |
| WO | 8807498 | A1 | 10/1988 |
| WO | 9953971 | A1 | 10/1999 |
| WO | 0128919 | A1 | 4/2001 |
| WO | 03103734 | A1 | 12/2003 |

OTHER PUBLICATIONS

PCT/EP2020/072884 International Preliminary Report on Patentability, Jul. 30, 2021.
P. Melnikov et al., Gallium-containing hydroxyapatite for potential use in orthopedics, Materials Chemistry and Physics 117 (2009) 86-90.
Japanese First Office Action dated Jun. 4, 2024, relating to JP Patent Application No. 2021-572842.
Chinese Office Action & Search Report dated Feb. 28, 2023, relating to CN Patent Application No. 202080044666.0.
Russian Office Action & Search Report dated Nov. 25, 2022, relating to RU Patent Application No. 2022103409/04(007284).

* cited by examiner

*Primary Examiner* — David J Blanchard
*Assistant Examiner* — Daniel F Coughlin
(74) *Attorney, Agent, or Firm* — DINSMORE & SHOHL L.L.P

(57) ABSTRACT

The invention relates to a method for producing an osteotropic bone replacement material from a starting material which substantially has portlandite, calcium oxide, aragonite; calcite and/or apatite. The starting material is introduced into an autoclave with a strontium, fluorine and/or gallium source, wherein when using a starting material which substantially has portlandite, calcium oxide, aragonite; calcite a phosphate source is introduced. In addition, $H_2O$ is added into the autoclave as part of a solvent and the pH value in the autoclave is set to a range above 7. Afterwards, the closed and filled autoclave is heated for at least 1 hour and then cooled. The osteotropic bone replacement material thus developed is subsequently cleaned from residues of the phosphorus, strontium, fluorine and/or gallium source. Furthermore, the invention relates to an osteotropic bone replacement material which substantially consists of apatite and in which strontium ions are incorporated into the crystal lattice.

9 Claims, 3 Drawing Sheets

OSTEOTROPIC BONE REPLACEMENT

Figure 1:
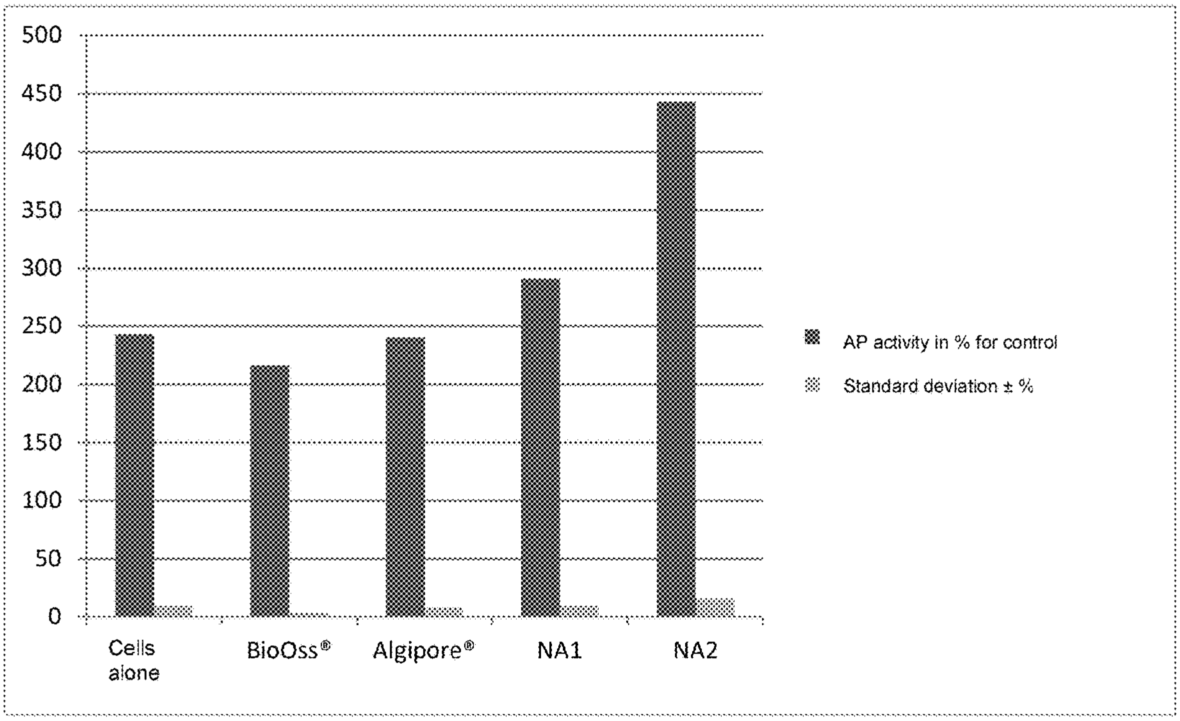

The invention relates to a method for producing an osteotropic bone replacement material from a starting material which substantially has portlandite, calcium oxide, aragonite, calcite, for example skeletons of lime-encrusting algae, and/or apatite, for example as hydroxyl apatite, e.g. from vertebrate bones or produced synthetically. Furthermore, the invention relates to an osteotropic bone material produced according to the method pursuant to the invention.

Within the framework of the invention the stated starting materials can also be understood as materials that have a structure analogous to the starting materials, yet being produced synthetically.

Many bone replacement materials in current used that consist of natural bone, both autologous, allogeneic and xenogeneic, corals, algae or also hydroxyl apatite bone replacement materials produced in a fully synthetic manner which are employed as bone implant or as bone replacement material within the framework of bone augmentations have osteoconductive properties only. This means indeed that the hitherto employed calcium phosphate or hydroxyl apatite bone replacement materials have a suitable biocompatible surface for direct growth of bone tissue on the implant surface, however they do not directly stimulate the formation of new bone in the direct bone environment of the implant. Hydroxyl apatite or calcium phosphate materials are generally only osteoconductive. Hence, they enable bone growth but do not by themselves stimulate the proliferation or differentiation of cells doing bone mount, such as osteoblasts or their progenitors. Within the meaning of the invention direct growth can in particular be understood as growth without "intermediate tissue layer" between the implant surface and bone tissue.

To deploy an osteoinductive effect bone replacement materials or also organic substances, such as collagens or organic molecules, have so far been supplemented with further proteins, peptides or other molecules. Examples for this are growth factors, such as various BMPs, IGF1/2, FGF or the like, or serum products. The problem with this is that these substances often remain for an indistinct period of time in the implant or at the implant location because in many cases they are quickly flushed out of the implant site or degraded. As a result, the osteoinductive properties are on the one hand only present for a short amount of time and cannot really be dosed, on the other hand systemic effects in the entire organism are also possible that are generally not intended.

Examples for production methods for such a bone replacement material can be taken from the European patents EP 230 570 B1 and EP 028 074 B1. In this case, a bone replacement material consisting of hydroxyl apatite that originates from lime-instructing marine algae is obtained by converting the naturally present calcium carbonate skeleton in a suitable manner.

However, as already set out such a bone replacement means is solely osteoconductive and not osteoinductive.

Furthermore, from P. Melnikov et al., Materials Chemistry and Physics 117(1), 86-90, (2009) gallium-containing hydroxy apatite for use in orthopedics, from CN 101928136 A fluoridated hydroxy apatite and its use for the production of artificial bones and from EP 2 228 080 A a gallium-doped phospho-calcic compound with apatite structure to fill tooth or bone defects can be taken.

The invention is therefore based on the object to provide a method for producing a bone replacement material and a bone replacement material itself which has long-active, localized osteotropic properties.

In accordance with the invention this object is achieved by a method for producing an osteotropic bone replacement material having the features of claim 1.

Advantageous embodiments of the invention are stated in the subclaims.

According to the invention provision is made in that a starting material is used which substantially has portlandite, calcium oxide, aragonite, calcite and/or apatite, e.g. as hydroxyl apatite. The starting material is introduced into an autoclave together with a strontium, fluorine and/or gallium source, wherein when using a starting material which substantially has portlandite, calcium oxide, aragonite; calcite a phosphate source is introduced. In the case of a starting material which substantially consists of apatite a phosphate source can also be introduced, however, this is not obligatory. In addition, water is added into the autoclave as part of a solvent. Afterwards, at room temperature and normal pressure, the pH value in the autoclave is set to a range above 7. The closed and filled autoclave is then heated for at least one hour and cooled subsequently. Finally, the content of the autoclave is cleaned from residues of the strontium, fluorine and/or gallium source. The same also applies to the phosphorus source if used.

According to the invention the realization was made that, among others, strontium, fluorine and/or gallium ions which are incorporated into an apatite structure have osteoinductive or rather osteotropic or antiresorptive properties.

Here, an essential aspect of the invention is the method pursuant to the invention in order to incorporate rather than just attach the strontium, fluorine and/or gallium ions in a suitable manner in apatite, in particular in a hydroxyl apatite structure. In the case of a purely superficial attachment a detachment of the attached substances might occur. However, through the method according to the invention it is rendered possible that the above-mentioned ions that have osteotropic, i.e. osteoinductive, antiresorptive properties and/or those promoting the installation of bone tissue, are bound to the developing apatite structure in such a way that these cannot be detached without further ado.

For a successful conversion of the starting materials consisting of calcium carbonate materials, i.e. in particular portlandite, calcium oxide, aragonite, calcite, into apatite or rather a hydroxyl apatite structure the presence of a phosphate source is essential, in which case different phosphate salts can be employed. When using an apatite material as starting material, for instance vertebrate bones, the presence of a phosphate source is not absolutely necessary but is advantageous. In particular, this prevents the existing structure from being weakened during the method.

According to the examinations underlying the invention particularly good results could be achieved if the closed and filled autoclave is heated to at least 30° C., preferably to over 190° C. This can take place in an oven or a heating module. It is also possible to provide a heating module integrated with the autoclave. At these temperatures a sufficiently good conversion of the starting material into doped apatite is accomplished wherein in addition, as already outlined, the stated ions are incorporated and bound to the crystal lattice of the apatite. The lower the temperature of the oven, the slower is the reaction taking place in the autoclave.

Within the meaning of the method according to the invention a heating cabinet or the like can also be referred to as oven. What is essential in conjunction with this is the fact that the appliance is able to maintain a desired temperature between 30 and several hundred degrees constant over a longer period of time.

To clean the content of the autoclave from residues of the strontium, fluorine and/or gallium source as well as the phosphorus source different methods are possible. Depending on the choice of the sources the content of the autoclave can preferably be cleaned mechanically using a filter apparatus. This is the case if sources are used that are as large or as hardly soluble as possible.

For good tissue tolerance of the bone replacement material according to the invention it is advantageous if, following a cleaning that is in particular mechanical, the content of the autoclave is cleaned until a pH value below 8 is reached.

To set the pH value before closing the autoclave to a range above 7 an alkaline solution, in particular an ammonia solution, can be used. For example, an ammonium dihydrogen phosphate solution or also another phosphate compound can be used for this purpose.

The introduction of a strontium, fluorine and/or gallium source is preferred in excess in relation to the starting material. Advantageously, this also applies to the phosphate source. In other words, a large reservoir of the respective materials is made available so that a good incorporation into the crystal lattice of the apatite can be achieved with high certainty. In the final, previously described cleaning step the respective unused starting substances of the strontium, fluorine and/or gallium source as well as the phosphorus source are removed from the produced material. This means that the material is cleaned.

When using e.g. ammonium dihydrogen phosphate or diammonium phosphate as phosphorus source this means can at the same time be used to set the desired pH value. It has also turned out that the use of ammonium dihydrogen phosphate dissolved in water is especially easy to dose and an optimum reaction environment can be achieved in the autoclave.

By preference, in the total mixture in the autoclave calcium and phosphorus atoms are present at a ratio not exceeding 10:5. Such a ratio has proved to be advantageous for the osteotropic properties of the resulting bone replacement material since the respective osteotropic, i.e. osteoinductive substances and/or materials having an antiresorptive effect are present at a ratio that provides especially good results.

As apatite use can be made of vertebrate or mammal bones for example. Mammal bones, e.g. from cattle or hogs, already provide apatite with a considerable proportion of hydroxyl and carbonate apatite. On the other hand, as starting material aragonite or calcite, calcareous algae skeletons or other calcium carbonate materials in burnt, unburnt and/or chemically treated form can also be employed. When using vertebrate or mammal bones these are advantageously previously subjected to a pyrolytic or chemical maceration, i.e. the removal of immunogenic material.

Basically, a longer heating of the closed and filled autoclave is preferred. According to the invention it has been found that after 1 to 4 days very good results of the developing osteotropic bone replacement material are achieved so that an even longer heating does not necessarily lead to significantly better results.

As already set out, after heating in the autoclave and subsequent cooling the strontium, fluorine and/or gallium source is separated from the resulting osteotropic bone replacement material by cleaning the latter. Here, it is preferred that as strontium, fluorine and/or gallium source a material easy to wash out or of poor water solubility is used.

The use of a material easy to wash out has the advantage that when washing the produced osteotropic bone replacement material it can be washed out easily and thus the osteotropic bone replacement material can be cleaned more easily. Alternatively, a material of poor solubility, in particular of coarsely crystalline nature, has the advantage that during the conversion process in the autoclave a sufficient amount of strontium, fluorine and/or gallium ions are available, though a subsequent cleaning can take place in a particularly easy way, for example also mechanically.

Particularly, easy cleaning of the resultant osteotropic bone replacement material can be achieved if the strontium, fluorine and/or gallium source is added into the autoclave as solid matter in a container. Here, the container is designed such that it enables the exchange of ions of the strontium, fluorine and/or gallium source with the solvent present in the autoclave while the solids are retained. This clearly facilitates the final cleaning of the resultant osteotropic bone replacement material.

It is preferred if prior to or after introduction into the autoclave the starting material and/or the content of the autoclave, following completion of the method, is subjected to a pyrolytic treatment and/or a chemical cleaning. The pyrolytic treatment and the chemical cleaning method respectively have the advantage that potentially existing proteins or other organic foreign substances are removed from the produced osteotropic bone replacement material so that interactions on implantation of the bone replacement material into a human body are minimized or excluded respectively.

Furthermore, the invention relates to an osteotropic bone replacement material produced according to the previously described method pursuant to the invention. The osteotropic bone replacement material which substantially has apatite contains strontium, fluorine and/or gallium ions in its crystal lattice. These unfold osteotropic properties after implantation into an animal or human body. In addition to apatite, more particularly hydroxyl apatite, small parts of calcium phosphate, calcite, aragonite and tricalcium phosphate can also be present. According to the invention the medium concentration of the ions, in the case of the strontium ions, lies above a medium concentration to the amount of approximately 0.51 to 0.60% by weight as known from known bone replacement materials from vertebrate or mammal bones (BioOss® (Geistlich®), The Graft® (Regedent®), Miner-Oss® XP (Camlog®/BioHorizons®): approximately 0.51-0.56% by weight) and lime-encrusting algae (Algipore® (Symbios®): approximately 0.60% by weight) or also from the natural bone of vertebrates or mammals (cattle: approximately 0.58% by weight), in particular also due to impurities, supplementary feeding or also the different geological-regional conditions. According to the invention the medium concentration of the strontium ions amounts in this case to at least 0.65% by weight, preferably to 0.75% by weight, in particular even more than 1.0% by weight.

The osteotropic bone replacement material according to the invention produced pursuant to the method according to the invention can be used for example for the production of dimensionally stable blocks, in which tooth cylinder implants or other metal objects are also integrated. These blocks can be implanted in a jaw bone as future tooth implant supports and, following a healing phase of 3 to 6 months, can be directly used without a further secondary intervention. Due to the fact that the resulting osteotropic bone replacement material has a powder-like form the dimensionally stable blocks produced therefrom can be made to measure and thereby be adapted to bone defects such as a tooth gap.

As a result of the embedding of the strontium, fluorine and/or gallium ions in accordance with the invention the bone replacement material unfolds without further addition a local osteotropic effect which mainly and substantially only occurs at the implant site. Hence, the bone replacement material according to the invention has no systemic effect.

Another advantage resides in the fact that the bone replacement material according to the invention unfolds its osteoinductive or osteotropic effects over the entire period of time it remains at the implant site, and will only cease as soon as it is replaced by autochthonous bone tissue. In this way, a quicker and more sustainable bone healing of a bone defect is achieved.

Another example of application for the osteotropic bone replacement material according to the invention can be the stabilization in the case of osteoporotic, traumatic and/or malignant tumor-related vertebral fractures or vertebral compression fractures. Another possibility is to use the material produced according to the invention as starting material for 3-D printing methods.

The invention is explained in greater detail hereinafter by way of schematic exemplary embodiments with reference to the Figures, wherein show FIGS. 1 to 6 results of the comparative tests

PRODUCTION METHOD

In the following an exemplary production of the osteotropic bone replacement material according to the invention pursuant to the method according to the invention is described.

For this purpose, a Teflon container with a capacity of 150 ml is used. This is filled with the following substances:

| | | |
|---|---|---|
| Burnt algae material | 19.822 | g |
| Ammonium dihydrogen phosphate | 26.38 | g |
| Strontium fluoride | 2.212 | g |
| Potassium fluoride | 2.212 | g |
| Ammonia solution (25%) | 50 | ml |
| Deionized $H_2O$ | 50 | ml |

As starting material a skeleton of lime-encrusting algae is used as an example for aragonite. When using starting materials containing $CO_2$ it is usually advantageous if these are burnt, in which case preservation of the external structure of the material is desirable. As described, however, the method according to the invention can also be applied to an apatite material e.g. from vertebrate bones as starting material, in which case the presence of a phosphate source has proved to be advantageous on the one hand for the introduction of the osteotropic ions and on the other hand, however, also for preserving the structure of the starting material.

Before being added into the Teflon container the algae skeleton is cauterized so that any foreign proteins, proteins or the like are removed. Furthermore, ammonium dihydrogen phosphate, strontium fluoride, potassium fluoride and a 25 percent ammonia solution are added. In addition, deionized water is also added.

The respective weights or respectively the volumes of the added substances can be gathered from the table.

In the present case, ammonium dihydrogen phosphate serves as phosphate source, wherein, as set out, other phosphate sources are possible too. Strontium fluoride is used as strontium source and as fluorine source, too. Potassium fluoride is also employed as fluoride source.

After the substances have been introduced into the Teflon container and a possible gas formation has been awaited the said container is closed. Afterwards, the Teflon container is placed into an autoclave, e.g. into a pressure digestion container. This container is preferably made of stainless steel. Subsequently, the cover is screwed tightly so that an autoclave is created.

The correspondingly firmly closed pressure digestion container is then placed into a preheated heating cabinet or a heating block that has a temperature of 190° C.

The pressure digestion container remains in the heating cabinet for 5 days wherein the temperature of 190° C. is maintained. After expiration of this time the heating cabinet is switched off. The pressure digestion container then cools down slowly in the heating cabinet or respectively in the heating block. This takes approximately one day.

Following complete cooling-down the pressure digestion container and the Teflon container are opened and the resultant osteotropic bone replacement material is cleaned. For this purpose, the osteotropic bone replacement material is applied together with water onto a filter paper and washed. Several cleaning processes, e.g. rinsing processes, are carried out until a pH value below 8 is reached.

Subsequently, the osteotropic bone replacement material is again introduced into the heating cabinet but only dried at 40° C.

Afterwards, the osteotropic bone replacement material is ready for further use. For instance it can then be brought into desired shapes and sterilized.

Tests and Results

In the following the effect of the new osteotropic bone replacement material produced according to the method pursuant to the invention is explained in greater detail and respectively the osteoinductive effectiveness is proved on the basis of test results. The results show that by the bone replacement material according to the invention the local formation of new bone in the bone defect should be additionally stimulated due to the fact that the most important bone formation marker in human bone cells, the alkaline phosphatase, is stimulated.

In vitro tests with primary human osteoblastic bone cells were carried out to examine the direct influence of the osteotropic bone replacement material according to the invention when in contact with primary human cells. This was also carried out to avoid overlooking detrimental influences of the osteotropic bone replacement material according to the invention on human bone cells that would involve cell death.

Hence, before clinical use of new bone replacement materials in vivo primary human osteoblastic bone cells are suitable as sensitive test system to examine the effect of a novel bone replacement material on human bone cell metabolism.

A cell in vitro—thus also a primary human bone cell—has four possible ways of reaction:

- no reaction at all
- apoptosis (cell death)
- increased/reduced cell division
- increased/reduced production of differentiated cell products (for example alkaline phosphatase in the case of bone cells) that are necessary for the build-up of new bone tissue and for the mineralization and formation of hydroxyl apatite in vivo.

To carry out the tests co-cultures of primary human bone cells were used. In order to compare the effect commercially available bone replacement materials and osteotropic bone replacement material produced according to the method pursuant to the invention were used. In the in vitro experiments the following bone replacement materials were comparatively tested with regard to their effect on primary human bone cells:

1. BioOss® (bovine bone granulate, commercially distributed by Geistlich Biomaterials)
2. Algipore® (based on EP 230 570 B1, commercially distributed by Dentsply)
3. New Algipore 1 (=NA1) osteotropic bone replacement material according to the invention
4. New Algipore 2 (=NA2) osteotropic bone replacement material according to the invention
5. New BioOss1 (BioOss® which was subjected to the method according to the invention)

| | NA1 | NA2 | BioOss1 |
|---|---|---|---|
| Starting material [g] | 7.21 | 7.51 | 0.5 |
| Duration [h:min] | 116.9666667 | 221.75 | 116 |
| Ammonium hydrogen phosphate [g] | 10 | 10.001 | 10.0521 |
| Potassium fluoride [g] | 0.4 | 0.821 | 1.996 |
| $SrF_2$ [g] | 0.35 | 0.688 | 0.821 |
| Ammonia solution 25% [g] | 6 g | 50.278 | 18.183 |
| $H_2O$ | filled up to 75% | filled up to 75% | filled up to 75% |
| Autoclave volume [ml] | 57.7 | 57.7 | 57.7 |

The following determination methods were chosen to examine the influence of the above materials on cell functions of primary human bone cells:

a. Alkaline phosphatase
b. Cell protein

1. Test

Alkaline Phosphatase

The comparative results are expressed in % of the control+/−standard deviation. Initially, the activity of alkaline phosphatase was examined in the medium supernatant after culture of the human bone cells in the presence of the different materials. As control served an aliquot of the employed cell culture growth medium by itself without cells because in the cavities of the culture plates always remain residues of the serum contained in the culture medium despite serum-free rinsing prior to the exposition of the cells with the materials. The serum also always contains small amounts of alkaline phosphatase. In this first test the new BioOss1 had not yet been available.

| Cells alone | BioOss ® | Algipore ® | NA1 | NA2 |
|---|---|---|---|---|
| 243 +/− 9% | 216 +/− 3% | 240 +/− 8% | 291 +/− 9% | 443 +/− 15% |

These results are illustrated graphically in FIG. 1.

Interpretation

BioOss® is prone to reduce the activity of the enzyme alkaline phosphatase which is indispensable for the mineral and bone formation of human bone cells, whereas the bone replacement material according to the invention brings about a highly significant increase in the activity of alkaline phosphatase secreted by human bone cells.

Thus, the bone-specific alkaline phosphatase as the most important osteoblast marker protein is stimulated by the bone replacement material according to the invention to a extreme significantly stronger degree in the human bone cell model than in the presence of the conventional materials. The different effectiveness of NA1 and NA2 on alkaline phosphatase activity can be ascribed to an increased fluoride and strontium content in NA2 as compared to NA1.

When measuring the activity of alkaline phosphatase in the cell culture supernatant account must be taken of the fact that also in vivo the mineral or bone formation takes place extracellularly through secretion of alkaline phosphatase into the osteoblastic microenvironment.

Cell Division/Cell Protein

As an indication of an effect of the bone replacement materials on cell division the protein content in the individual "cavities", i.e. reaction chambers of the employed multi-perforated plates was analyzed. For this, a triton extract of the respective cavities was used to determine the protein content according to the BCA method. The higher the protein content in the individual cavities, the more cell material that corresponds to protein material must be present in the cavities. This means that the cell count has increased since a bone cell always has a similar size and proteins are not stored to a larger extent intracellularly in bone cells. A reduction of the protein content in a cell culture cavity, i.e. a reaction chamber, would therefore be tantamount to a reduction of the cell count located adherently on the cell culture base or on the bone replacement materials (apoptotic cells, i.e. dead cells, do not stay adherent and are flushed away before the addition of triton). The results are again stated in % of the control+/−standard deviation.

| Cells alone | BioOss ® | Algipore ® | NA1 | NA2 |
|---|---|---|---|---|
| 96 +/− 3% | 108 +/− 4% | 103 +/− 3% | 103 +/− 3% | 103 +/− 3% |

Figure 2:
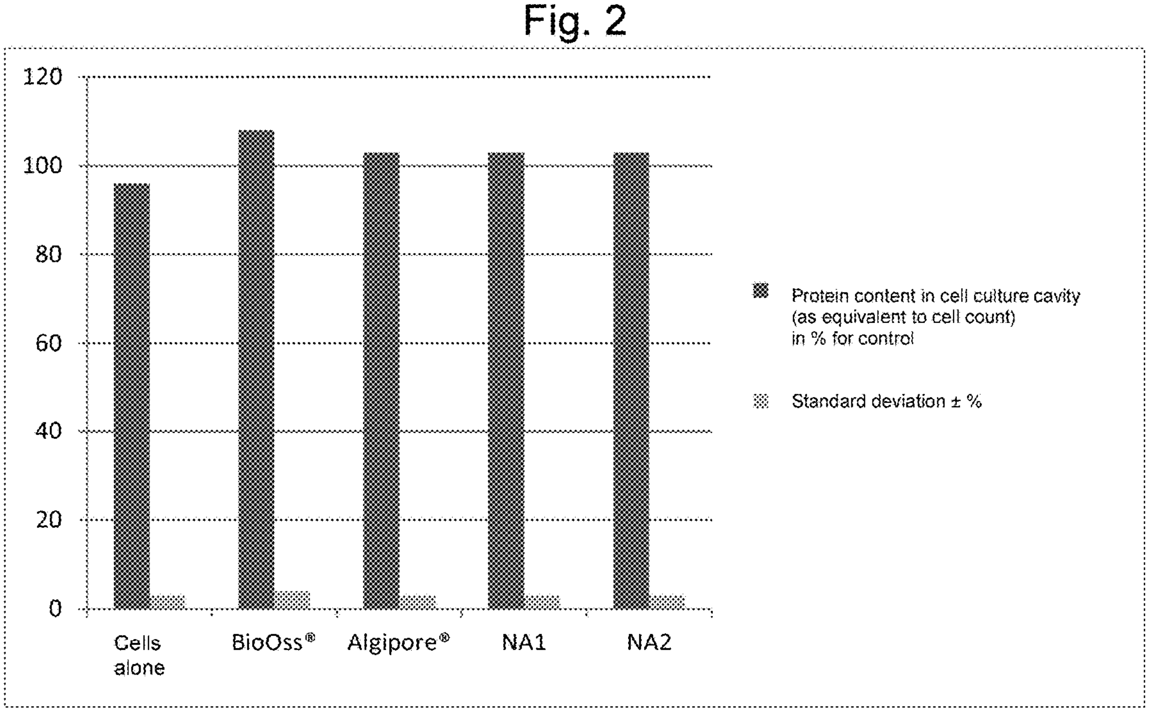

These results are illustrated graphically in FIG. 2.

Interpretation

There is no difference between the examined materials with regard to the cell protein content in the cell culture cavities. Hence, the materials do not have an impact on cell division, nor on cell death, because apoptotically degenerating cells do not stay adherent but become detached and would be flushed away prior to the assay method.

Overall View

These observations indicate that the materials obtained according to the method pursuant to the invention have a very positive effect on the alkaline phosphatase activity of human bone cells.

This observation is consistent with a very favorable and sustained effect of the bone replacement material according to the invention stimulating bone mineral formation in vivo without cell division being impacted, i.e. stimulated or inhibited.

2. Test, Activation of the Conventional BioOss® Material by the Method According to the Invention The material BioOss® hitherto employed as bone replacement material in dental medicine or oral surgery consists of natural hydroxyl apatite material of inorganic bone tissue of cattle. By way of the method according to the invention, even in the case of a natural calcium phosphate crystal lattice, a partial exchange of calcium ions in the hydroxyl apatite crystal with strontium and fluoride ions can be carried out in a controlled manner. In this case, calcium and phosphorus atoms should be present at a ratio not exceeding 10:5 in the total mixture of the autoclave net weight.

In the following experiment with primary human osteoblastic cells the effect of the conventional BioOss® material on alkaline phosphatase activity is examined in parallel to the effects of the BioOss1 material activated by the method according to the invention.

At the same time the materials already tested above were also used in the same experiment in order to allow a ranking of the effectiveness of all materials produced by way of the method according to the invention in a parallel test approach. In this case, too, the alkaline phosphatase activity in the cell culture supernatant was measured after an incubation time of the cells with the new material 24 hours.

This experiment was again carried out with primary human bone cells of a different individual than in the first experiments (1. test).

Alkaline Phosphatase

| Cells alone | BioOss ® | BioOss1 | Algipore ® | NA1 | NA2 |
|---|---|---|---|---|---|
| 393 +/− 19% | 368 +/− 16% | 645 +/− 20% | 431 +/− 24% | 418 +/− 9% | 747 +/− 51% |

Figure 3:
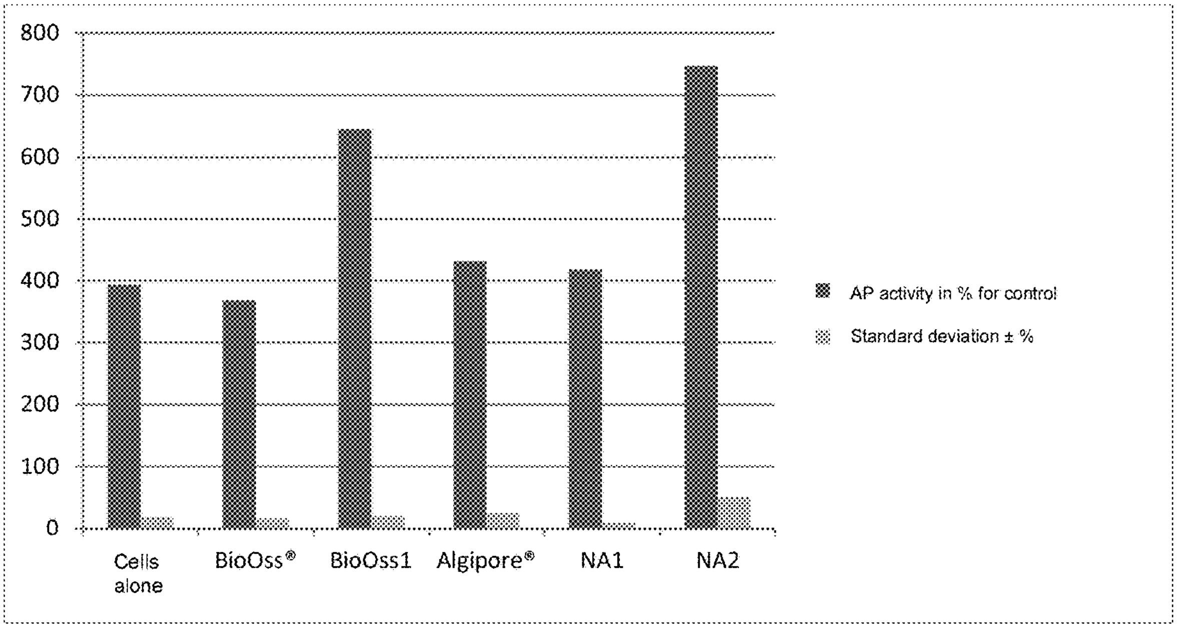

These results are illustrated graphically in FIG. 3.

Cell Division/Cell Protein

| Cells alone | BioOss ® | BioOss1 | Algipore ® | NA1 | NA2 |
|---|---|---|---|---|---|
| 96 +/− 5% | 106 +/− 5% | 97 +/− 3% | 93 +/− 6% | 98 +/− 3% | 107 +/− 5% |

Figure 4:
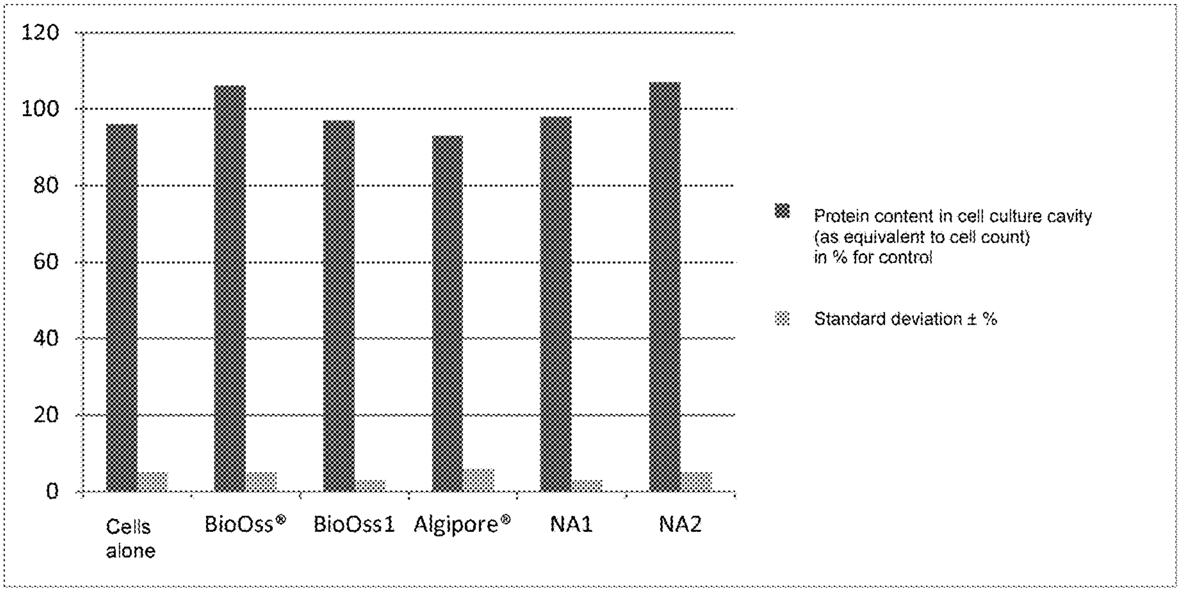

These results are illustrated graphically in FIG. 4.

Interpretation

While the conventional BioOss® material has no significantly stimulating effect on the alkaline phosphatase activity in the cell culture supernatants as compared to human bone cells without contact to a bone replacement material, the BioOss® material (BioOss1) pretreated by way of the method according to the invention brings about almost a doubling of alkaline phosphatase activity. Therefore, the method according to the invention is also suitable for activating commercially available bovine hydroxyl apatite material and lends osteoinductive properties to the BioOss® material that has so far only been of osteoconductive nature.

Furthermore, this experiment reproduces the results of the first test already analyzed above: Commercial BioOss® shows no substantial stimulation of alkaline phosphatase while BioOss1 produced by way of the method according to the invention shows an activation of alkaline phosphatase activity that is almost twice as strong. Likewise, the "algae hydroxyl apatite materials" NA1 and in particular NA2 produced by way of the method according to the invention show an even more potent stimulation of alkaline phosphatase activity.

In this comparative experiment there is again no reliable indication as to a significantly different effect of the tested bone replacement materials on cellular total protein production in the cell supernatants in the reaction chambers (see FIG. 4).

3. Test, Reproduction of the Results

In another approach all experiments are once more repeated with different primary human osteoblastic cells of a third healthy donor and the results are reproduced in a consistent manner. Hence, in this case the effects of all materials hitherto produced according to the method pursuant to the invention are again reproduced in parallel in a further test approach and compared with the effects of commercially available bone replacement materials.

The alkaline phosphatase activities were again measured in the cell culture supernatants in the reaction chambers.

Alkaline Phosphatase

| Cells alone | BioOss ® | BioOss1 | Algipore ® | NA1 | NA2 |
|---|---|---|---|---|---|
| 566 +/− 32% | 488 +/− 14% | 708 +/− 18% | 683 +/− 31% | 683 +/− 61% | 867 +/− 63% |

Figure 5:
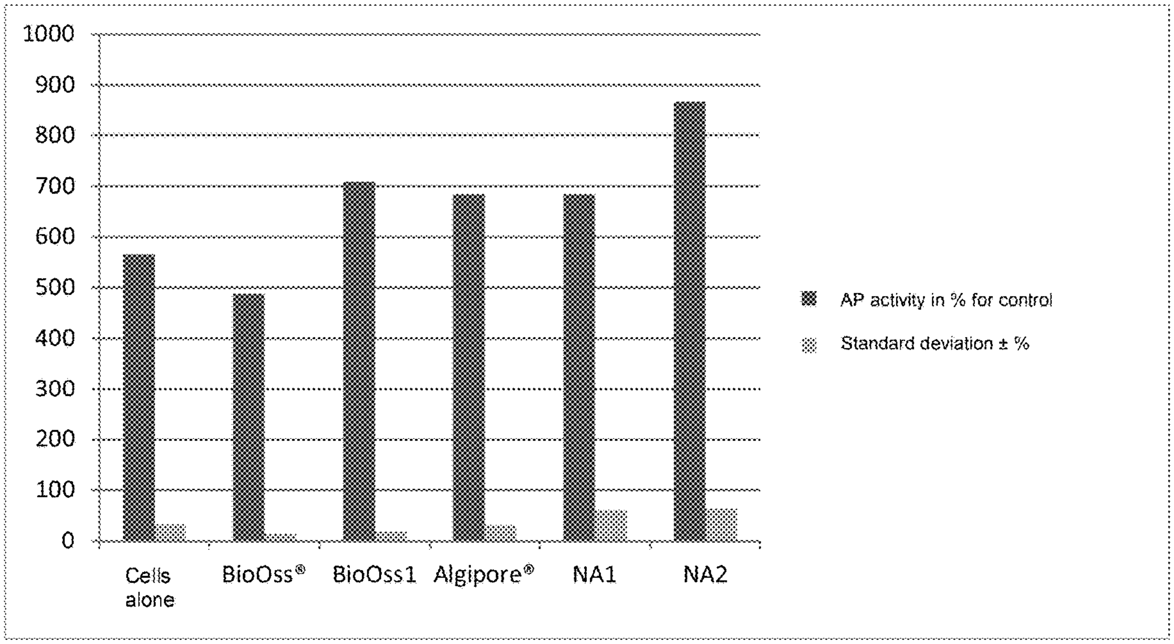

These results are illustrated graphically in FIG. 5.

Cell Division/Cell Protein

| Cells alone | BioOss ® | BioOss1 | Algipore ® | NA1 | NA2 |
|---|---|---|---|---|---|
| 96 +/− 5% | 113 +/− 4% | 98 +/− 5% | 103 +/− 3% | 100 +/− 7% | 102 +/− 3% |

Figure 6:
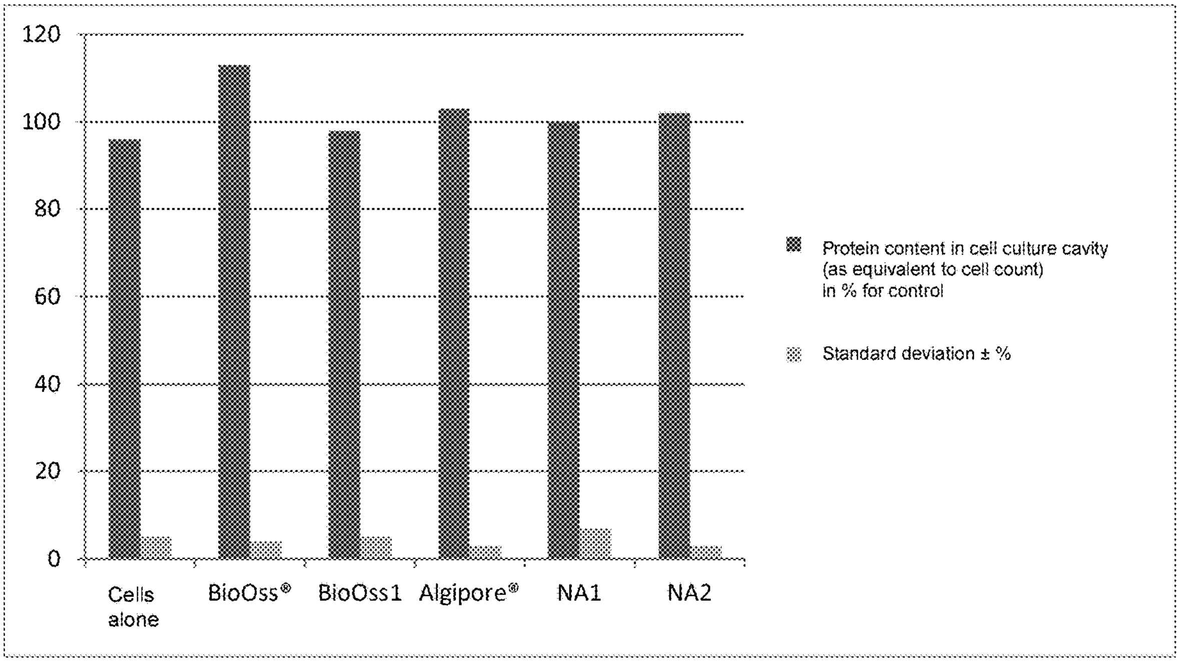

These results are illustrated graphically in FIG. 6.

Interpretation

In this experiment, too, the bone replacement materials NA2 and BioOss1 "activated" by the method according to the invention prove to be of significantly stronger effect as to the stimulation of alkaline phosphatase activity than the commercially available bone replacement materials BioOss® and Algipore®. The NA1 material treated in an initial process shows an effect comparable to the commercially available Algipore® bone replacement material.

Consequently, every bone replacement material "activated" by the production method according to the invention proves to be superior to the previous products with regard to the stimulation of the osteoblastic standard bone formation marker alkaline phosphatase.

The production method according to the invention is therefore suitable to produce an activated bone replacement material both during a conversion process from a calcium carbonate or respectively a mixture of portlandite, calcium oxide and calcite into an apatite material and directly from an existing hydroxyl apatite material by incorporating activated ions, such as strontium ions, into the crystal lattice. Within the framework of the invention a material can in particular be considered as activated that has osteoinductive or respectively osteotropic or also antiresorptive properties.

Consequently, by the method according to the invention and respectively accordingly by the osteotropic bone replacement material produced using the method according to the invention a material is provided that has long-acting and localized osteoinductive or respectively osteotropic properties and is excellently suitable as implant material in bone tissue.

The invention claimed is:

1. Method for producing an osteotropic bone replacement material from a starting material which has portlandite, calcium oxide, aragonite; calcite and/or apatite, wherein portlandite, calcium oxide, aragonite and/or calcite are used in the form of burnt, unburnt and/or chemically treated biogenic skeletons and/or wherein as apatite vertebrate bones after pyrolytic or chemical maceration are used, the method comprising:

adding a strontium, fluorine and/or gallium source as solid matter into a container containing a solvent for treatment in an autoclave, wherein the solvent at least partially dissolves the solid matter to produce strontium, fluorine, and/or gallium ions which are available for ion exchange with the starting material, while undissolved solids are retained within the container;

adding the starting material into the container with the strontium, fluorine and/or gallium source, wherein the apatite is synthetic or natural and/or wherein when using a starting material which has portlandite, calcium oxide, aragonite and/or calcite, a phosphate source is introduced;

adding $H_2O$ into the container as part of the solvent, placing the container in the autoclave, wherein the pH value in the autoclave is set to a range above 7, wherein the autoclave is heated to a temperature in a range of 30° C. to 300° C. for a duration of at least twelve hours and then cooled, and wherein subsequently the content of the autoclave is cleaned from residues of the phosphorus, strontium, fluorine and/or gallium source, thereby obtaining an osteotropic bone replacement material comprising apatite in which one or more of strontium, fluorine and gallium ions are incorporated into the crystal lattice.

2. Method according to claim 1, characterized in that the content of the autoclave is cleaned mechanically using a filter apparatus.

3. Method according to claim 1, characterized in that the content of the autoclave is washed with $H_2O$ until a pH value of smaller than 8 is reached.

4. Method according to claim 1, characterized in that to set the pH value in the autoclave to a range above 7 an alkaline solution is used.

5. Method according to claim 1, characterized in that as phosphorus source ammonium dihydrogen phosphate or diammonium phosphate is added.

6. Method according to claim 5, characterized in that in the total mixture calcium and phosphorus atoms are present at a ratio not exceeding 10:5 (atomic ratio).

7. Method according to claim 1, characterized in that the closed and filled autoclave is heated for at least 12 hours.

8. Method according to claim 1, characterized in that prior to or after introduction into the autoclave the starting material and/or the content of the autoclave is subjected to a pyrolytic treatment and/or a chemical cleaning method.

9. A method for producing an osteotropic bone replacement material from a starting material which substantially has portlandite, calcium oxide, aragonite, calcite and/or apatite, wherein portlandite, calcium oxide, aragonite and/or calcite are used in the form of burnt, unburnt and/or chemically treated biogenic skeletons and/or wherein as apatite vertebrate bones after pyrolytic or chemical maceration are used, wherein a strontium, fluorine and/or gallium source is added into an autoclave as solid matter in a container, in that the container enables the exchange of ions of the strontium, fluorine and/or gallium source with a solvent, wherein solids are retained, wherein the starting material is added into the container with the strontium, fluorine and/or gallium source, wherein when using a starting material which has portlandite, calcium oxide, aragonite, and/or calcite, a phosphate source is introduced, wherein $H_2O$ is added into the container as part of the solvent, wherein the pH value in the autoclave is set to a range above 7, wherein the closed and filled autoclave is heated for at least 1 hour and then cooled, and wherein subsequently the content of the autoclave is cleaned from residues of the phosphorus, strontium, fluorine and/or gallium source.

* * * * *